United States Patent [19]

Miyamura et al.

[11] Patent Number: 5,734,019
[45] Date of Patent: Mar. 31, 1998

[54] HEPATITIS C VIRUS ANTIGEN POLYPEPTIDE, PRODUCTION METHOD THEREFOR, AND ANTIBODY DETECTION METHOD

[75] Inventors: Tatsuo Miyamura; Izumu Saito, both of Tokyo; Shizuko Harada, Shinagawa; Yoshiharu Matsuura, Saitama; Joe Chiba, B-26-4, 626, Endoh, Fujisawa-shi, Kanagawa, 252, all of Japan

[73] Assignees: National Institute of Health, Tokyo; Joe Chiba, Fujisawa, both of Japan

[21] Appl. No.: 952,543

[22] PCT Filed: May 29, 1991

[86] PCT No.: PCT/JP91/00724

§ 371 Date: Dec. 11, 1992

§ 102(e) Date: Dec. 11, 1992

[87] PCT Pub. No.: WO91/19744

PCT Pub. Date: Dec. 26, 1991

[30] Foreign Application Priority Data

Jun. 12, 1990 [JP] Japan ..................... 2-154542

[51] Int. Cl.⁶ .................. C07K 14/18; C12N 15/51; G01N 33/569
[52] U.S. Cl. .................. 530/350; 530/826; 435/69.3; 435/5; 930/223
[58] Field of Search .................. 530/350, 826; 930/223; 435/5, 69.3

[56] References Cited

U.S. PATENT DOCUMENTS 5,032,511  7/1991  Takahashi et al. .............. 435/69.1
5,350,671  9/1994  Houghton et al. .............. 435/5

FOREIGN PATENT DOCUMENTS 0318216    5/1989  European Pat. Off. ........ C12N 15/00
0 388 232  9/1990  European Pat. Off. .
0419182    3/1991  European Pat. Off. ........ C12N 15/51
2-500880   3/1990  Japan .
9002206    3/1990  WIPO ..................... C12Q 1/68

OTHER PUBLICATIONS

Miller et al. Proc. Natl Acad Sci USA vol. 87 pp. 2057–2061 (1990).
Muraiso et al., "A structural protein of Hepatitis C virus expressed in *E. coli*," Biochem Biophys Res Comm. 172:511–516 (1990).
Journal of General Virology, vol. 71, No. 12, 1990, K. Takeuchi, et al., "The Putative Nucleocapsid and Envelope Protein Genes of Hepatitis C Virus Determined By Comparison of The Nucleotide Sequences of Two Isolates Derived From An Experimentally Infected Chimpanzee and Healthy Human Carriers", pp. 3027–3033.
Science, vol. 244, Apr. 21, 1989, Qui–Lim Choo, et al., "Isolation of a cDNA Clone Derived from a Blood–Borne non–A, non–B Viral Hepatitis Genome", pp. 359–362.
The Lancet, vol. 335, 1990, A.J. Weiner, et al., "Detection of Hepatitis C Viral Sequences In non–A, non–B Hepatitis", pp. 1–3.
Chiba et al., *Proc. Natl. Acad. Sci. USA*, v. 88, pp. 4641–4645, 1991.
Okamoto et al., *Japan J. Exp. Med.*, 1990, 60(3):167–177.
Hijikata et al., *Proc. Natl. Acad. Sci. USA*, v. 88, pp. 5547–5551, 1991.

*Primary Examiner*—Michael P. Woodward
*Attorney, Agent, or Firm*—Oblon, Spivak, McClelland, Maier & Neustadt, P.C.

[57] ABSTRACT

A hepatitis C virus antigen polypeptide having a molecular weight of approximately 22 kilodaltons expressed from a hepatitis C virus structural gene region; a production method for a hepatitis C virus antigen polypeptide having a molecular weight of 22 kilodaltons and/or a peptide related thereto, wherein an expression vector having inserted thereinto a cDNA fragment of a hepatitis C virus structural gene region is inserted into a cultured cell line and the transfected cell line thus obtained is cultured; and a detection method for a hepatitis C virus antibody, wherein a hepatitis C virus antigen polypeptide is used as an antigen, and an antibody specific thereto is detected.

2 Claims, 2 Drawing Sheets

HEPATITIS C VIRUS ANTIGEN POLYPEPTIDE, PRODUCTION METHOD THEREFOR, AND ANTIBODY DETECTION METHOD

DETAILED DESCRIPTION OF THE INVENTION

1. Technical Field

The present invention relates to a novel antigen which is useful in the diagnosis of the hepatitis C and the like and is translated from the structural region of the hepatitis C virus genome, a production method therefor, and a detection method for antibodies associated with hepatitis C using this antigen.

In greater detail, the present invention relates to a novel HCV antigen polypeptide (hereinafter termed "p22") which is a peptide which is coded for in the hepatitis C virus (hereinbelow termed "HCV") structural gene region and which exhibits a molecular weight in SDS-PAGE of roughly 22 kilodaltons, a production method for this HCV antigen polypeptide, and a detection method for antibodies associated with hepatitis C using this polypeptide.

2. Prior Art

HCV has recently been identified as a pathogenic virus causing hepatitis C, which is one type of vital hepatitis. It is characteristic in that it is responsible for almost all cases of hepatitis C occurring after blood transfusions in Japan, and in that it causes not only transient infection but also persistent infection (in Japan, about 1.2% of the population is persistently infected). Approximately half of all cases of acute hepatitis C become chronic, and furthermore, chronic hepatitis may gradually develop into cirrhosis or liver cancer. In addition, the percentage of those who are persistently affected is reported to be from 1–3% of the population worldwide. That is to say, hepatitis C is a grave infectious disease worldwide, and the prevention, early diagnosis, and treatment thereof have global significance.

HCV is a positive strand RNA virus;the virus genome thereof has a size of approximately 10,000 bases. A structural gene region coding for the viral structural protein is located on the 5' side of the genome, and a non-structural (NS) gene region is located downstream from this. No antigen protein coded for by this virus has been identified as yet. The sole measuring method for antigens and antibodies which has been reported to date is an antibody (anti-C100 antibody) detection method for a fusion protein (C100) which is produced in yeast and contains 363 amino acids of a part of the HCV non-structural gene region (a region from NS3 to NS4). Using this antibody detection method, it is possible to determine, to a certain extent, whether a history of exposure to HCV exists, so that this detection method has been used in the diagnosis of the hepatitis C virus. Furthermore, blood which registers positive on this detection test often contains infectious HCV, so that this detection method is presently in use in Japan in the screening of blood to be used in transfusions.

Problems to Be Solved by the Invention

The C100 antibody described above normally takes from 3–6 months to become positive after the infection of hepatitis C virus, so that this method cannot be used as a diagnostic method for hepatitis C during this period, and this has been recognized to be a major problem. Furthermore, even in cases in which only blood which was negative for the anti-C100 antibody was used in blood transfusions, a certain number of occurrences of the hepatitis C virus was noted, so that it is thought that only approximately half of hepatitis cases occurring after blood transfusions could be screened out by using this method alone; there is thus a need for a new antibody test or a detection method for virus structural protein antigens. Furthermore, as the C100 antigen is derived from non-structural protein genes, identification of a virus structural protein and establishment of a detection system for the antigens and the antibodies thereof is extremely important in order to find a more direct diagnostic method or candidates for future vaccines.

Means Used to Solve the Problems and Effects of the Invention

As a result of conducting research in order to solve the above problems, the present inventors have expressed the cDNA of the HCV structural gene region in cultured cells, and, by means of the fluorescent antibody technique and the Western blot method using the serum of hepatitis C patients, have discovered a novel polypeptide (p22) which is derived from an HCV gene, has a molecular weight of approximately 22 kilodaltons, and which reacts specifically with the serum of hepatitis C patients, and by separating this, have arrived at the present invention.

Next, a method was developed for the extraction and purification of the HCV-related antigen p22 from a novel cell line obtained by means of transfecting a cultured cell line with an expression vector having inserted thereinto the cDNA fragment of the HCV structural gene region used above and cloning the cultured cell line, and furthermore, a method was developed for the extraction, purification, and efficient production of HCV p22 in large amounts in cultured cell systems by means of transfecting cells of a cultured cell line Sf from a cutworm moth with a Baculovirus expression vector having inserted thereinto the cDNA fragment of this HCV structural gene region.

Furthermore, using the HCV p22 obtained in this manner, an ELISA kit for the detection of the p22 antibody was constructed, and it was determined that this was greatly superior to the conventional HCV antibody measurement method.

Furthermore, the present invention provides not merely the p22 having a molecular weight of approximately 22 kilodaltons described above, but also an HCV-related polypeptide having a larger molecular weight and characterized by containing this complete peptide as a part thereof, a production method therefor, and an HCV antibody detection method using this.

BEST MODE FOR CARRYING OUT THE INVENTION

Figure 1:
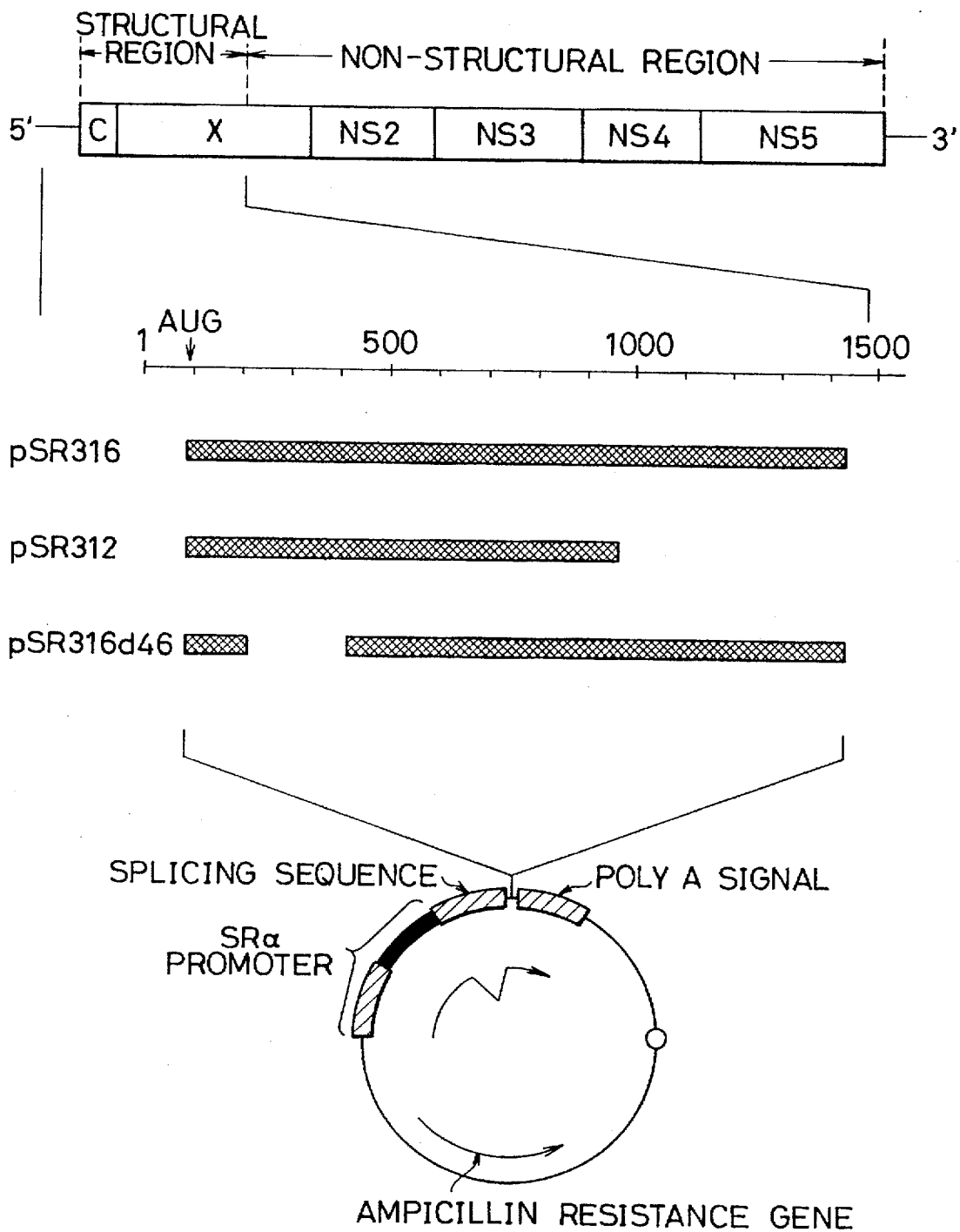
FIG. 1 is a plasmid structural diagram showing the regions on the HCV genome of the HCV-cDNA fragment integrated into the expression plasmids pSR316, pSR312, and pSR316d46.

Hereinbelow, detailed explanation will be given concerning the p22 and p22-related polypeptides, the production method thereof, and the detection of HCV antibodies using these antigens of the present invention.

(1) p22

From experimental results such as the genetic configuration of the related Flaviviruses, the fact that the proteins thereof are rich in basic amino acids, and the fact that they have no N-sugar chain, it is believed that the p22 of the present invention is a nucleocapsid protein which is one of the hepatitis C virus structural proteins. Judging from the example of the related Flaviviruses, it is believed that the structural protein of HCV is produced by being cut from a precursor protein with an enzyme (signalase) which is present in animal and insect cells.

As a result of the research of the present inventors, it was discovered that the p22 of the present invention is a polypeptide produced by means of the processing in the cell of a precursor polypeptide of HCV which is coded for by the HCV structural gene. As a result of this, it is believed that the p22 of the present invention is a polypeptide which is identical to the original nucleocapsid protein of HCV, and it is thought to be an extremely important antigen for the detection of HCV-related antibodies. Furthermore, the antigen of the present invention is an important material not merely for the detection of this type of antibody, but also for the production of a vaccine for the purpose of preventing HCV infection.

From the expression experiments of the present inventors using various HCV cDNA fragments, it is conjectured that the p22 of the present invention is a polypeptide which is positioned at the N-terminus (amino terminus) of the extremely long HCV precursor polypeptide for which the HCV gene codes. Furthermore, on the basis of the base sequence, it is presumed that this polypeptide is hydrophilic and is rich in basic amino acids.

Furthermore, the amino acid region which is from approximate the 180th to the 190th amino acid, counting from the initial amino acid (methionine) of the above precursor polypeptide has an amino acid sequence which is particularly strongly hydrophobic, so that it is believed that the amino acids of this region are recognized by signalase, and the polypeptide of the present invention is produced by being cut from the precursor polypeptide.

(2) Production Method of p22 and Related Peptides

The p22 of the present invention can be obtained in large amounts by means of the expression in cultured cells of the cDNA of the the HCV structural genetic region. It is possible to use, as the cultured cells which function as the host cells, animal cells such as COS cells or CHO cells, which are in common use, and the present invention may be carried out according to standard transformational methods and culturing methods.

On the other hand, in the case in which E. coli or a yeast, which do not possess signalase identical to that of animal cells, are used as the expression hosts, only the genetic region coding for p22 is put into an open reading frame form in advance, and expression can be conducted so that there is no need for processing after expression. However, in the case in which expression is conducted using cDNA which is longer than the genetic region which codes for the p22 polypeptide, it is believed that processing by means of signalase cannot be achieved, so that it is not believed that p22 can be easily expressed by means of expression in E. coli or a yeast.

In order to yet further efficiently express p22, it is possible to use a Baculovirus as a vector, and to introduce this into insect cells.

Any virus which is classified as a Baculovirus may be used as this type of virus vector; for example, Autographa Californica, *Trichoplusia ni, Rachiplusia ou, Galleria mellonella*, or *Bombyx mori*. Among these viruses, Autographa Californica (referred to in short as AcNPV) is preferred.

In the production of a recombinant virus, a first recombinant vector incorporating DNA regions which are not necessary for the multiplication of the Baculovirus is first produced. In this case, it is necessary to place, in this region, a promoter which functions in the Baculovirus, and it is preferable to insert a synthetic linker having an appropriate restriction enzyme cleavage sequence downstream from this promoter.

Here, references to DNA regions which are not necessary for multiplication refer to regions which have no substantial effect on the multiplication of the virus even if they received mutations as a result of the insertion of exogenous DNA, such as, for example, the polyhedrin gene of the Baculoviruses [L. K. Miller, et al., Science, 219, pp. 715–721 (1983)] and the like.

In this connection, it has been shown that polyhedrin is a protein with a molecular weight of approximately 29,000 daltons and that the gene thereof is present in the Eco RI fragment of the AcVPV genome [G. E. Smith, et al., J.Virol., 45, pp.215–225 (1983)], and the DNA sequence of the polyhedrin gene was disclosed in the paper of G. E. Smith, et al., [Virology, 131, pp. 561–565 (1983)].

Furthermore, with regard to promoters which function within Baculoviruses, any base Sequence, whether synthesized or naturally occurring, which is capable of effectively functioning as a promoter in a transcription system possessed by a Baculovirus may be used; concrete examples thereof include, for example, a gene promoter coding for a polyhedrin of a Baculovirus, a Baculovirus gene promoter coding for a 10K polypeptide, and the like.

In order to increase the expression amount, it is preferable to use a vector in which the polyhedrin gene promoter, the 5' non-translated region of the polyhedrin gene, a restriction enzyme cleavage sequence which is added immediately after the 5' non-translated region and the 3' non-translated region of the polyhedrin gene are connected in this order and in which the polyhedrin structural gene sequence is completely removed. It has been shown that the expression amount of exogenous genes becomes extremely large with this type of vector [Matsuura, et al., J. Gen. Virol., 68, pp. 1233–1250 (1987); Japanese Unexamined Patent Application, No. (Hei) 1-285198].

The cDNA of the HCV structural gene region used in the present invention was previously isolated by the present applicants (U.S. patent application Ser. No. 408,045), and furthermore, this type of HCV gene fragment has been deposited at the Fermentation Research Institute by the present applicants (pS7-28c: FERM BP-2638; pS1-713c: FERM BP-2637; and pU1-1216c: FERM BP-2594), and it is possible to use these gene fragments as representative starting material.

The HCV-cDNA integrated into the expression vector may be an DNA fragment containing at least a section from the translation initiation codon (ATG: methionine) of the precursor polypeptide coded for in the HCV genome to approximately the signalase recognition site (the 180th to 190th amino acid, counting from methionine).

Furthermore, even in the case in which a longer section of cDNA, for example, genes coding for up to approximately the 400th amino acid, counting from methionine, is expressed in cultured cells, it is possible to conduct processing within host cells and to obtain the desired p22.

In this manner, at the time of the expression of p22 in cultured cells, in the case in which a large gene is used as the HCV structural gene to be integrated, a polypeptide having a larger molecular size and possessing the amino acids of the p22 peptide of the present invention is partially obtained as a by-product. A specific reaction with blood serum from human hepatitis C patients has also been confirmed, in the case of an HCV antigen containing this type of p22 peptide and having a larger molecular weight. That is to say, the present invention provides an HCV antigen having a larger molecular weight and possessing the p22 polypeptide as a portion thereof. With respect to the molecular weight of this polypeptide, the molecular weight varies in accordance with the length of the HCV-cDNA which is integrated; for example, in the case in which HCV-cDNA having methionine as the N-terminus and coding for 289 amino acids is used, a polypeptide of approximately 35 kilodaltons is obtained, and furthermore, in the case in which HCV-cDNA coding for 441 amino acids is used, a polypeptide of approximately 50 kilodaltons is obtained.

(3) Detection of an HCV-related antibody using a recombinant HCV structural protein containing p22

By means of the use of the recombinant HCV structural protein of the present invention as an antigen, it is possible to detect the HCV antibody which is specific thereto, and it is possible, by means thereof, to make an early diagnosis of hepatitis C, which was not conventionally possible.

It is possible to use a common enzyme immunoassay (EIA), RIA, immunofluorescent technique, agglutination technique, or the like as the measurement method.

That is to say, by means of the present invention, an antibody detection method was established with respect to p22 derived from the HCV structural gene, and diagnosis from blood sera and tissue samples has thus become possible.

The p22 antibody cannot be detected in the blood sera of a healthy person, a hepatitis A patient, or a hepatitis B patient, and furthermore, the tendency for a positive result at a considerably earlier stage of hepatitis C infection has been recognized, so that a detection method for the detection of this antibody can be used for the early diagnosis of hepatitis C and for the screening of blood for transfusions.

Hereinbelow, the present invention will be explained in detail with reference to examples; however, the present invention is in no way limited to these examples.

EXAMPLES (1) Construction of an Expression Plasmid in a COS Cell

The HCV structural gene was previously cloned by the present inventors by means of the reverse transcription PCR method from Japanese non-A and non-B hepatitis pathogen carriers, and this was made on the basis of U.S. Pat. No. 5,372,928.

cDNA which was integrated into pS7-28c, pS1-713c, pS1-713g, and pU1-1216c plasmids was used in the expression of the HCV antigen protein of the present invention. Using conventional methods, the base sequences of the common portions of these 4 cDNA sections were cleaved with restriction enzymes, and by means of recombining with other clones, a plasmid pS7/1-216 containing the cDNA of the entirety of these clones connected together was created. The accession numbers of each plasmid used and the various gene fragments which were used (cloned) in the plasmid pS7/1-216 which was constructed are shown.

| PLASMID | ACCESSION NUMBER | FRAGMENT USED |
|---|---|---|
| pS7-28c | FERM BP-2638 | 5' terminus -BsU 36I |
| pS1-713g | None | Bsu 36I-Sal I |
| pS1-713c | FERM BP-2637 | Sal I- Dde I |
| pU1-1216c | FERM BP-2594 | Dde I-3' terminus |

Furthermore, the HCV base sequence regions integrated into each plasmid, and the region integrated into the plasmid pS7/1-216 which was constructed, are shown below. The numbers used for the bases refer to the case in which the initial base of the Japanese HCV cDNA of the plasmid pS7-28c is given the number "1".

| PLASMID | HCV REGION | INTEGRATED REGION |
|---|---|---|
| pS7-28c | 1-572 | 1-518 |
| pS1-713g | 501-1100 | 519-874 |
| pS1-713c | 501-1100 | 875-1083 |
| pU1-1216c | 1063-1413 | 1084-1413 |

The pS1-713g plasmid has not been deposited; however, in comparison with the pS1-713c plasmid, the G (guanine) at the 627th base is replaced by an A (adenine), and the T (thymine) at the 1041st base is replaced by a C (cytosine), and the amino acid sequence which is coded for is identical in the case of both cDNA fragments.

The pS7/1-216 sequence prepared in this manner contains the 1413 bases of the HCV cDNA from Japanese patients, and at the 3' end thereof, a Bam HI linker and an Eco RI linker are attached. In this cDNA, an open reading frame exists which occupies almost the entire length thereof, and at the 91st base thereof, an ATG sequence, which is thought to be a translation initiation codon, was located.

Next, this pS7/1-216 sequence was cleaved at the Acc I site located 12 bases upstream from the translation initiation codon, and then a Pst I linker was attached thereto. Next, a further Kpn I linker was added at the Eco RI site which was attached to the 3' end of the cDNA, the cDNA was recovered as a Pst I-Kpn I fragment, and this was cloned at the Pst I-Kpn. I site of the expression vector pcDL-SRα 296 [Yutaka Takebe, et al., Mol. Cell Biol., 8, 466–472, (1988)] in a cultured cell system. This expression vector was developed by Takebe and colleagues, and comprises a strong promoter, splicing sequence, and polyA sequence. The expression plasmid pSR316 was prepared in this manner (see FIG. 1).

Using pSR316 as a base, 2 types of plasmids which lacked a portion of the HCV structural gene, pSR312 and pSR316d46, were prepared (see FIG. 1).

A section was removed to prepare the pSR312 plasmid by means of cutting with Eco RI downstream from the Pvu I site at the 957th base of the HCV cDNA sequence and the subsequent synthesis of a new strand and bonding with polymerase.

In the pSR316d46 plasmid, the 201 bases from 210–411 are deleted by means of the partial cutting of the HCV cDNA sequence at the Apa I sites at the 210th and 411th bases and ligating with a ligase. In this case, the translation frame of the HCV cDNA is maintained, and it is believed that a deletion of 67 amino acids is caused.

(2) Expression of p22 in COS Cells 20 micrograms of each of the above 3 plasmids were transfected by means of a calcium phosphate method into $2 \times 10^6$ COS-1 cells of a cultured cell line from simian kidney cells [Y. Gluzuman, Cell, 23,pp. 175–182 (1981)]. After 2 days, using the blood serum of chronic hepatitis C patients, the antigens were stained by means of an immunofluorescence technique following normal methods. Furthermore, on the same day, intracellular proteins were detected by means of Western blot method and using the above-described blood serum of chronic hepatitis C patients.

During the immunofluorescence technique, in approximately 10% of the cells, antigens which were localized in the cytoplasm and which were stained in a fine granular form were observed. This fluorescence was detected in equal degrees when the pSR316 and pSR312 plasmids were used; however, in the case of the pSR316d46 plasmid, almost no fluorescence was detected, and furthermore, only in the case of the vector pcDL-SRα 296, into which no HCV-cDNA was integrated, was no fluorescence detected.

Figure 2:
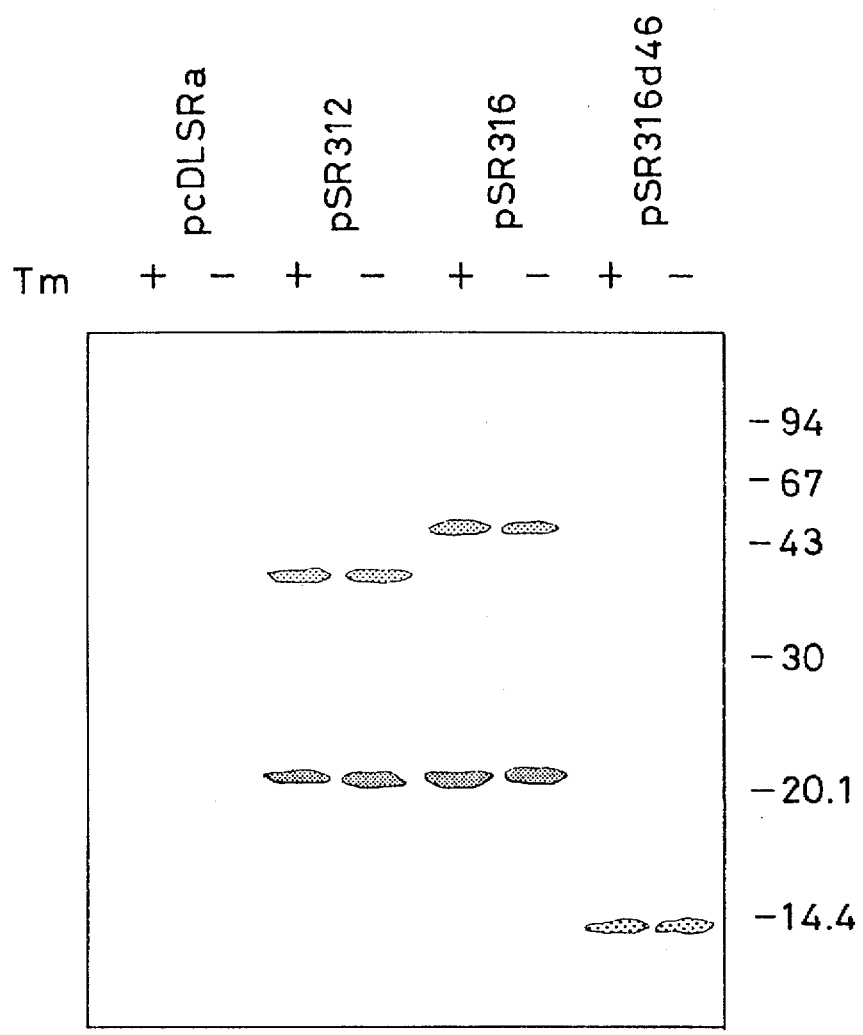
FIG. 2 is a schematic diagram showing the results of the Western blot of the endoproteins of a cell transformed with the various plasmids of Example (2). The "+" symbol indicates a sample which was treated with tunicamycin (Tm), while the "−" symbol indicates a sample which was not treated with Tm.

When the pSR316 plasmid was used in the Western blot method, a protein having a molecular weight of 22 kilodaltons was detected as an extremely thick band (see FIG. 2). This band was also detected in the case of the pSR312 plasmid; however, it was not detected in the case of the pSR316d46 plasmid or in the case of the vector pcDL-SR α 296, so that it is believed that this represents detection of the antigen which was observed using the immunofluorescence technique. Irrespective of the fact that the length of the translatable region from the Japanese HCV-cDNA which was used was 441 amino acids in the case of the pSR316 plasmid, and 289 amino acids in the case of the pSR312 plasmid, the fact that the molecular weight of the main protein which was detected was 22 kilodaltons is believed to be caused by the processing of the proteins within the COS cells after the translation of these proteins. The same types of mechanisms have been observed in the proteins of the structural gene regions of the Flaviviruses, which are believed to be related to this virus [C. M. Rice, et al., Science, 229, pp. 726–733 (1985)], and it is believed that the precursor peptide translated from this gene was cleaved with the enzyme signalase within the cells.

From the fact that p22 was detected in the case of the pSR316 and pSR312 plasmids, but not in the case of the pSR316d46 plasmid, it is believed that the region coding for p22 lies between the initial Met (methionine) of the amino acid sequence, and the 289th amino acid therefrom, and it is further believed that the region lacking in the pSR316d46 plasmid is included in this code region. Furthermore, a signal peptide type sequence is observed which comprises a series of hydrophobic amino acids from the 180th to the region of the 190th in the amino acid sequence which is coded for, and it is conjectured that this is the signalase cleaving recognition site. Furthermore, in the pSR316d46 plasmid, a 14 kilodalton protein was detected as a weak band; however, it is believed that this represents the detection of a protein which is shortened by 67 amino acids as a result of a deletion of 201 bases from the original p22.

Furthermore, in the Western blots, with respect to minor proteins other than p22, a band was detected at approximately 50 kilodaltons when the pSR316 plasmid was used, and a band was detected at approximately 35 kilodaltons when the pSR312 plasmid was used. From the fact that these bands correspond nearly exactly to the sizes of the proteins of the complete code regions of the HCV peptides contained in the plasmids, it is believed that these bands represent, in all likelihood, precursor proteins translated from the full length of the cDNA used in the expression.

(3) Expression Using a Baculovirus

The ends of a cDNA fragment (AccI site cleaved-EcoRI) which is identical to that used in the construction of the pSR316 plasmid were made blunt by means of polymerase processing, and a pAC316 plasmid was constructed by means of cloning the cDNA fragment at the Bam HI site of a pACYM1 plasmid [Matsuura, et al., J. Gen. Virol., 68, pp. 1233–1250 (1987)] having ends which were made blunt by means of the same polymerase.

After this, this plasmid was co-transfected together with Baculovirus DNA into cultured cells from an insect [Spodoptera frugiperda cells], and a recombinant Baculovirus was isolated following normal methods.

Sf cells were transfected with this virus in MOI10, and the expression of p22 was determined after 72 hours had elapsed. $1\times10^4$ transfected cells were migrated using SDS-PAGE (SDS-polyacrylamide gel electrophoresis), and after this, when staining was conducted with Coomassie Brilliant Blue (CBB), a 22 kilodalton protein was detected as an expression protein. This band was not detected in the original Baculovirus-transfected cells into which the HCV cDNA was not integrated. Furthermore, in the immunofluorescence technique in which the blood serum of chronic hepatitis C patients was used, fluorescence which was specific to the cytoplasm was detected in 100% of the transfected cells. In the detection by means of the Western blot method, a 22 kilodalton protein was detected in this expression system as a main expression product. From the fact that the apparent molecular weight of this protein does not vary as a result of the addition of tunicamycin, which is identical to the case of COS cells, it is believed that the N-sugar chain is not attached. Furthermore, it is clear that the isoelectric point is extremely basic, so that the 22 kilodalton protein which was detected here cannot be distinguished within the parameters of the detection method from the p22 which was identified in the COS cells.

(4) HCV Antibody Detection Method Using a Recombinant HCV Structural Protein

HCV structural protein expressing cells (AeHCV-SF9) which were infected with the above recombinant Baculovirus were recovered, were rinsed twice with PBS, and then were suspended in 50 mM of Tris-hydrochloride buffer (pH 8.0) having added thereto 2 mM of EDTA and 0.1 mM of DTT so as to create a density of of $5\times10^6$ cells/ml.

This cellular suspension fluid was lysed by sonication, and by means of centrifugal processing (12000×G, 20 minutes, 4 degrees Celsius) the clear supernatant thereof was recovered. To this was added saturated ammonium sulfate so as to reach 33% saturation, centrifugation was again conducted, 1 ml of PBS was added to the precipitate fraction thereof per $5\times10^6$ cells, this was dissolved by sonication, and HCV antigen protein was obtained by means of decanting. This was maintained in a frozen state at a temperature of −80 degrees Celsius, and in the case in which this was to be used as an antigen for an immunoassay, it was coated onto an ELISA plate immediately after ultrasonic processing.

The above crudely produced HCV antigen was diluted 50 times with PBS, and 100 microliters of this was added to each of the wells of a 96 well microtiter plate, this was stored overnight at a temperature of 4 degrees Celsius, and the ELISA plate was thereby coated.

This plate was twice washed with PBS-Tween, 200 microliters of PBS containing 3% skim milk was added to each well, this was incubated for 1 hour at room temperature, and blocking was thereby conducted.

100 microliters of the blood serum which was the object of the HCV antibody assay was placed in each well of the plate, and this was stored for 2 hours at room temperature.

This plate was washed 4 times with PBS-Tween, and to each well was added 100 microtiters of alkaline phosphatase-labeled goat anti-human immunoglobulin diluted with PBS-Tween with 3% skim milk added thereto, and this was incubated for 1 hour at room temperature.

This plate was then washed 4 times with PBS-Tween, and to each well was added 700 microliters of alkaline phosphatase substrate solution.

This was left to stand for 1–2 hours at room temperature, and when the A405 absorption of the positive reaction reached a value of approximately 1.5, the absorbance of all the wells was measured.

Using this assay, the blood sera of actual patients were tested, and the following results were obtained.

In 2 typical cases of post-transfusion a non-A, non-B hepatitis, blood was collected at intervals starting immediately after the onset of symptoms, and hepatic function tests, the test for the presence of anti-C100 antibodies, which is presently the only test agent for HCV antibodies, and tests for the presence of an antibody to the p22 peptide were conducted. During a 12 month period of observation, an increase in the p22 antibodies which was essentially simultaneous with an increase in the GPT value was noted, even in the case in which anti-C100 antibodies were not detected.

Furthermore, in the other cases, the anti-C100 antibodies increased 4 months after the transfusion; however, antibodies to p22 were detected 3 months prior to this, that is to say, nearly simultaneously with the onset of symptoms. A result identical to the detection of the antibody was achieved by means of Western blot method using the above protein.

Next, the blood sera of 5 healthy people and the blood sera of non-A, non-B hepatitis patients (of which 6 tested positive for the anti-C100 antibody and 4 tested negative for the anti-C100 antibody) were tested together. Of the healthy persons, none tested positive, while of the non-A, non-B hepatitis patients who tested positive for the anti-C100 antibody, 5 out of 6 tested positive, and of the non-A. non-B hepatitis patients who tested negative for the anti-C100 antibody, 4 out of 4 tested positive.

From the above results, the following has been confirmed.

① This antibody cannot be detected in normal subjects.
② 90% of non-A, non-B hepatitis cases test positive.
③ Even in cases of sera of the patients who were clinically diagnosed as non-A, non-B hepatitis which tested negatively for the anti-C100 antibody, approximately 100% test positive according to this method.
④ Even with blood serum which tests positive for the anti-C100 antibody, there are cases in which the test for this antibody is negative.

From these results, it has been confirmed that the antibody to p22 is specifically detectable in cases of present or past HCV infection. This antibody is induced at an early stage of infection, so that the detection thereof is extremely useful for an early diagnosis of hepatitis C.

What is claimed is:

1. A recombinant hepatitis C virus antigen polypeptide obtained by:

expressing pSR312 or pSR316 plasmid in COS cells, and isolating an expressed protein which has a molecular weight of approximately 22 kilodaltons, as determined by SDS-PAGE.

2. A recombinant hepatitis C virus (HCV) antigen polypeptide which has a molecular weight of approximately 22 kilodaltons as determined by SDS-PAGE, said antigen polypeptide is expressed from the hepatitis C virus structural gene region in animal cells transfected with HCV DNA, said HCV DNA comprises from the translation initiation codon of said structural gene region to at least the 180th amino acid encoded by said structural gene region, and said antigen polypeptide is specifically recognized by antibodies present in sera of HCV infected patients.

* * * * *